United States Patent [19]

Kawamata et al.

[11] 4,208,537
[45] Jun. 17, 1980

[54] PROCESS FOR THE SELECTIVE ORTHO-ALKYLATION OF PHENOLIC COMPOUNDS

[75] Inventors: Motoo Kawamata; Kazushi Ohshima; Akihide Kudoh; Makoto Kotani, all of Yokohama, Japan

[73] Assignee: Mitsui Toatsu Chemicals Incorporated

[21] Appl. No.: 964,262

[22] Filed: Nov. 27, 1978

[30] Foreign Application Priority Data

Oct. 31, 1977 [JP] Japan .................................. 52-129390
Dec. 6, 1977 [JP] Japan .................................. 52-145630
Dec. 26, 1977 [JP] Japan .................................. 52-155683
Jan. 26, 1978 [JP] Japan .................................... 53-6733

[51] Int. Cl.$^2$ ............................................. C07C 37/16
[52] U.S. Cl. ................................... 568/804; 568/789; 568/794
[58] Field of Search ................ 568/794, 785, 804, 789

[56] References Cited

U.S. PATENT DOCUMENTS

| | | | |
|---|---|---|---|
| 3,953,529 | 4/1976 | Yonemitsu et al. | 568/804 |
| 3,959,394 | 5/1976 | Tasaka et al. | 568/804 |

FOREIGN PATENT DOCUMENTS

| | | | |
|---|---|---|---|
| 2235389 | 2/1973 | Fed. Rep. of Germany | 568/790 |
| 49-36699 | 2/1974 | Japan | 568/790 |
| 51-12610 | 7/1976 | Japan . | |

*Primary Examiner*—Werren B. Lone

[57] ABSTRACT

The selective alkylation of a phenolic compound having a hydrogen atom in at least one of the ortho positions is achieved by reacting the phenolic compound with an alcohol in the vapor phase in the presence of a catalyst containing mixed oxides of chromium and tin. The catalyst can additionally contain iron oxide, sulfate radical, or a combination thereof.

16 Claims, No Drawings

PROCESS FOR THE SELECTIVE ORTHO-ALKYLATION OF PHENOLIC COMPOUNDS

BACKGROUND OF THE INVENTION (A) Field of the Invention

This invention relates to a process for the selective alkylation of the unsubstituted ortho position or positions of phenolic compounds. More particularly, it relates to a process for the selective ortho-alkylation of a phenolic compound by reacting the phenolic compound with an alcohol in the vapor phase in the presence of a catalyst containing mixed oxides of chromium oxide and tin oxide.

(B) Description of the Prior Art

The preparation of 2,6-dimethylphenol, among other ortho-alkylated phenols, has heretofore been the subject of many studies it is useful as a raw material for the manufacture of polyphenyleneoxide having a wide range of utility in the field of synthetic resins.

Currently, a process for the ortho-alkylation of phenols is in industrial use which involves the vapor phase reaction of a phenol with an alcohol in the presence of an acidic solid catalyst such as alumina. However, in this process, the selectivity in the site of alkylation is only limited. That is, not only the ortho positions of the phenolic nucleus but also the meta and para positions thereof are subject to alkylation, so that a complicated procedure for the separation and purification of desired reaction products if required.

Another industrial process for the ortho-alkylation of phenols is based on vapor phase reaction in the presence of a magnesium oxide catalyst. However, this catalyst has inherently low temperature activity and requires high temperatures of 475° C. or higher, practically 500° C. or higher, to achieve sufficient reaction. Moreover, its activity tends to become lower during a short period time of reaction.

In order to solve these problems, there have been proposed a number of catalysts including, for example, those comprising various combinations of magnesium oxide and another oxides, those comprising various combinations of iron oxide and other oxides, and the like. However, these catalysts still have the disadvantages that they are insufficient in selectivity for ortho-alkylation and in service life of the catalysts and that polyalkylated products such as 2,4,6-trialkylphenols are formed under reaction contitions suited for the enhancement of their insufficient activity. In addition, a chromium-iron mixed oxide catalyst is disclosed in Japanese Patent Publication No. 12610/'76. However, when phenol and methanol are used as starting materials, the yield of the desired product e.g. 2,6-dimethylphenol, is as low as about 40%. This makes the catalyst useless for practical purposes.

SUMMARY OF THE INVENTION

It is an object of the present invention to provide an improved process for the selective alkylation of the unsubstituted ortho position or positions of a phenolic compound.

It is another object of the present invention to provide a process for the ortho-alkylation of a phenolic compound with a high degree of conversion of the phenolic compound and a high degree of selectivity in the site of alkylation.

It is still another object of the present invention to provide a process for the ortho-alkylation of a phenolic compound which process involves the use of a catalyst having a sufficient activity at low temperature, a high degree of selectivity in the site of alkylation, and a long service life.

According to the present invention, there is provided a process for the selective alkylation of the ortho position of a phenolic compound having a hydrogen atom in at least one of the ortho positions by catalytically reacting the phenolic compound with an alcohol in the vapor phase, wherein the improvement comprises carrying out the reaction in the presence of a mixed oxide catalyst having chromium and tin included in the active substance thereof.

The catalyst containing the aforesaid chromium oxide and tin oxide as the active substance can further include iron oxide, sulfate radical, or a combination thereof.

DETAILED DESCRIPTION OF THE PREFERRED EMBODIMENTS

The phenolic compound which is used in the practice of the invention is one having a hydrogen atom in at least one of the ortho positions and can be represented by the formula

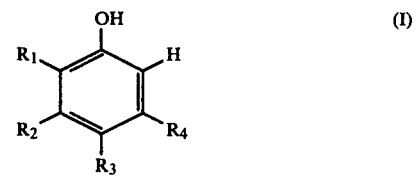

where $R_1$, $R_2$, $R_3$ and $R_4$ independently represent hydrogen atoms or saturated aliphatic hydrocarbon radicals having from 1 to 4 carbon atoms.

Specific examples of the phenolic compound of formula (I) include phenol; o-, m- and p-cresols; 2,3-, 2,4-, 2,5-, 3,4- and 3,5-xylenols; trimethylphenols; tetramethylphenols; o-, m- and p-ethylphenols; n-and iso-propylphenols; n-, iso- and tert-butylphenols; and the like. In addition, phenolic compounds having at least two different alkyl substituent groups on the same aromatic ring are also usable.

The alcohol which is used in the practice of the invention is a saturated aliphatic alcohol having from 1 to 4 carbon atoms. Specific examples of the alcohol include methyl alcohol, ethyl alcohol, isopropyl alcohol, n-propyl alcohol, n-butyl alcohol, isobutyl alcohol, tert-butyl alcohol, and the like.

One form of the chromium oxide and tin oxide containing catalyst which is used in the practice of the invention is a catalyst having an active substance essentially consisting of chromium oxide and tin oxide. The suitable composition of this catalyst is such that the Cr:Sn atomic ratio ranges from 100:0.1 to 100:60 and preferably from 100:1 to 100:20. If the tin content is below the aforesaid lower limit, the activity of the catalyst is reduced so that higher reaction temperatures are required. This results in a lowering of the selectivity for ortho-alkylation. On the other hand, if the tin content is above the aforesaid upper limit, the selectivity for ortho-alkylation is lowered and, moreover, the formation of by-products such as anisole is increased.

The aforesaid catalyst may be prepared by any of the conventional methods for the making of mixed metal oxide catalysts. However, satisfactory results cannot be obtained simply by mixing chromium oxide and tin oxide mechanically. It is desirable to achieve sufficiently intimate contact between both metal oxides by using such techniques as coprecipitation, gel kneading, impregnation, and the like. Several types of chromium oxide, such as $CrO$, $Cr_2O_3$ and $CrO_3$, are all useful in the practice of the invention. Amond these oxides, $Cr_2O_3$ is generally stable and capable of producing satisfactory results. Amond several types of tin oxide, $SnO_2$ is preferred for the same reason.

The chromium compound from which the chromium oxide is derived may be the oxides, bydroxides, halides, nitrates, sulfates and carbonates of chromium, ammonium chromate, and the like. Similarly, the tin compound from which the tin oxide is derived may be the oxides, hydroxides, halides, nitrates and sulfates of tin, and the like.

In the preparation of the catalyst, a chromium compound and a tin compound are mixed thoroughly by using a suitable technique such as coprecipitation, gel kneading, or the like, dried at a temperature below 150°, calcined at a temperature between 400° C. and 900° C., and then formed into pellets or orther desired shapes. Alternatively, a paste containing a chromium compound and a tin compound may be coated on a suitable carrier such as alumina, silica, steatite, carborundum, or the like, and then calcined.

The chromium oxide and tin oxide containing catalyst used in the invention, can further include iron oxide, sulfate radical, or a combination thereof as the active substance. As to the catalyst having an active substance composed of chromium oxide, tin oxide, and iron oxide, the suitable composition thereof is such that the Cr:Sn:Fe atomic ratio ranges from 100:0.1:0.01 to 100:60:20 and preferably from 100:1:0.1 to 100:20:10. If the tin and/or iron contents are below the aforesaid lower limits, the activity of the catalyst is reduced so that higher reaction temperatures are required. This brings the alkylation of undesired positions (other than the ortho positions), thus resulting in a lowering of the selectivity for ortho-alkylation. On the other hand, if the tin and/or iron contents are above the aforesaid upper limits, the selectivity for ortho-alkylation is lowered and, moreover, the formation of by-products such as anisole (which is an etherification product of phenol) is increases. The iron contained in this catalyst has the primary function of enhancing its activity. With this catalyst, the reaction temperature required to achieve a a desired degree of conversion can be reduced by about 30°–50° C., as compared with the case in which the corresponding iron-free catalyst is used. This served not only to improve the selectivity for ortho-alkylation of the phenolic compound but also to suppress any undesirable decomposition of the alcohol.

This catalyst can be prepared in a manner similar to that described for the mixed oxide catalyst of chromium and tin. $Fe_2O_3$ is preferred over other types of iron oxide, and the iron compound from which the iron oxide is derived may be the hydroxides, halides, mineral acid salts, organic acid salts, and other compounds of iron.

As to the catalyst having an active substance composed of chromium oxide, tin oxide, and sulfate radical, the suitable composition thereof is such that the Cr:Sn:S atomic ratio ranges from 100:0.1:0.25 to 100:60:20 and preferably from 100:1:0.5 to 100:20:10. If the sulfate radical content is above the aforesaid upper limit, the catalyst becomes so unstable that its activity is reduced in a very short period of time. Moreover, the formation of by-products such as anisole (which is an etherification product of phenol) is increased and the alkylation of undesired positions (other than the ortho positions) is increased to lower the selectivity for ortho-alkylation. The sulfate radical contained in this catalyst has the functions of enhancing its activity and prolonging its service life. With this catalyst, the reaction temperature required to achieve a desired degree of conversion can be reduced by about 30°–50° C., as compared with the case in which the corresponding sulfate-free catalyst is used. This serves not only to improve the selectivity for ortho-alkylation of the phenolic compound but also to suppress any undesirable decomposition of the alcohol.

The chromium oxide and tin oxide contained in this catalyst, as well as the chromium and tin compounds from which those oxides are derived, may be the same as described for the foregoing catalysts. The addition of sulfate radical can be accomplished either by using the sulfates of chromium and/or tin as starting materials, by incorporating sulfuric acid at any suitable stage of the process of preparing the catalyst, or by adding a suitable sulfonic acid to the catalyst being prepared.

This catalyst may be prepared by any of the conventional methods for the making of mixed metal oxide catalysts. For example, starting materials are mixed, a small amount of water is added thereto, and the resulting mixture is blended well in a kneader or mixer. Alternatively, starting materials are dissolved in water, a suitable basic compound is added thereto, and the coprecipitated insoluble products are mixed with an adequate amount of a compound containing sulfate radical or sulfonic group. It is also practicable to form a mixed oxide of chromium and tin from starting materials and then add thereto a compound containing sulfate radical. The resulting catalyst is usually dried at a temperature below 150° C., mixed with a suitable granulating additive or processing aid such as microcrystallite cellulose, starch, polyvinyl alcohol, or the like, formed into any desired shape by a suitable technique such as extrusion, compression molding, vibration, rolling, or the like, and then calcined to make it ready for use. Alternatively, the resulting catalyst may be directly calcined and crushed to make it ready for use.

As to the catalyst having an active substance composed of chromium oxide, tin oxide, iron oxide, and sulfate radical, the suitable composition thereof is such that the Cr:Sn:Fe:S atomic ratio ranges from 100:0.1:0.01:0.25 to 100:60:20:20 and preferably from 100:1:0.1:0.5 to 100:20:10:10. The iron and sulfate radical contained in this catalyst have the same functions as described previously.

This catalyst can be prepared in a manner similar to that described for the catalyst containing chromium oxide, tin oxide and sulfate radical.

In carrying out the reaction of a phenolic compound with an alcohol, these starting materials are suitably used in a molar ratio ranging from 1:1 to 1:15 and preferably from 1:1 to 1:7. In order that the reaction may proceed smoothly, the starting materials may be preferably diluted with an inert gas such as nitrogen or carbon dioxide and then fed to the reaction zone. It is also preferable to add a small amount of water to the starting materials and thereby carry out the reaction in the presence of water, because such water serves to prolong the service life of the catalyst and suppress any undesirable decomposition of the alcohol during the reaction.

The reaction is generally carried out at a temperature of from 250° C. to 550° C. The preferred temperature range varies according to the type of catalyst used. Specifically, the reaction temperature ranges from 300° C. to 550° C. and preferably from 350° C. to 500° C. for the chromium oxide-tin oxide catalyst; from 250° C. to 550° C. and preferably from 300° C. to 500° C. for the chromium oxide-tin oxide-iron oxide catalyst; and from 250° C. to 500° C. and preferably from 300° C. to 475° C. or the chromium oxide-tin oxide-sulfate radical and chromium oxide-tin oxide-iron oxide-sulfate radical catalysts. If the reaction temperature is higher than the mentioned above, the selevtivity for ortho-alkylation of the phenolic compound is lowered and, moreover, the formation of various high-boiling compounds (such as polymerization and cyclization products) from the phenolic compound is increased. On the other hand, if the reaction temperature is lower, the conversion of the phenolic compound is reduced. This makes the present process impractical because large amounts of unreacted starting materials and intermediate products must be recovered and recycled to the reaction zone.

The starting materials are preferably fed to the reaction zone at a gas space velocity of from 300 to 20,000 per hour. Generally, greater gas space velocities are used at higher reaction temperatures, and vice versa. The pressure of the reaction zone may be either atmospheric or super atmospheric. The reduced pressure can also be used. Although the reaction may be carried out according to any of the fixed bed, fluidized bed, and moving bed processes, a multitubular fixed-bed system is commonly used.

The present invention will be more clearly understood by reference to the following examples.

EXAMPLE 1

Five hundred g. of chromiun (III) nitrate nonahydrate and 20 g of tin (II) chloride dihydrate were dissolved in 10 l of water, and 5% aqueous ammonia was slowly added to this solution until its pH reached 7.0. The precipitated hydrogel was separated by filtration, washed with water, and then dried at 120° C. for about 5 hours. The dried gel was crushed and adjusted to a particle size of 6-12 mesh. Then, 120 ml. of the resulting catalyst (with a Cr:Sn atomic ratio of 100:11) was packed into a stainless steel tubular reactor having an internal diameter of 25 mm. An electric heater was used to externally heat the reactor through which nitrogen was being passed. Thus, the internal temperature of the reactor was kept at 450° C. for 5 hours and then reduced to 390° C. A mixture of phenol and methanol (in a molar ratio of 1:5) was passed through a preheating bed kept at 300° C. and then introduced into the reactor at a rate of 55 g per hour. The reaction product was cooled by passing it through a water-cooled condenser and then collected in a dry ice-acetone trap.

The product thus obtained was analyzed by gas chromatography. The conversion of the phenol was 99.9%. The selectivity based on the amount of phenol converted was 6.8% for o-cresol and 88.5% for 2,6-xylenol.

EXAMPLE 2

Two thousand g. of chromium (III) nitrate nonahydrate and 560 g of tin (II) chloride dihydrate were dissolved in 30 l of water, and 1,500 g of urea was added to this solution. The precipitate which was formed by boiling the solution was separated by filtration, washed with water, and then dried at 110° C. for about 6 hours. Using a pelletizing machine, the dried precipitate was formed into pellets having a diameter of 6 mm and a height of 3 mm. These pellets were placed in an electric over and calcined in air at 500° C. for 5 hours. Then, 200 ml of the resulting catalyst was packed into a reactor similar to that used in Example 1. The internal temperature of the reactor was kept at 350° C. for 2 hours, during which methanol was passed over the catalyst at a rate of 100 g per hour. After raising the temperature of the catalyst bed to 410° C., a mixture of phenol and methanol (in a molar ratio of 1:7) was introduced into the reactor at a rate of 130 g per hour.

The reaction product was collected and analyzed in the same manner as described in Example 1. The conversion of the phenol was 99.9%. The selectivity based on the amount of phenol converted was 5.3% for o-cresol and 92.7% for 2,6-xylenol.

EXAMPLES 3-9

Catalysts consisting of chromium oxide and tin oxide in various Cr:Sn atomic ratios were prepared in the same manner as described in Example 1. Using these catalysts, various mixtures of phenol and methanol were reacted at different temperatures. The results are summarized in Table 1.

Table 1

| Example No. | Composition of Catalyst (Cr:Sn Atomic Ratio) | Reaction Temperature (°C.) | Molar Ratio of Methanol to Phenol | Conversion of Phenol (%) | Selectivity (%) | |
|---|---|---|---|---|---|---|
| | | | | | o-Cresol | 2,6-Xylenol |
| 3 | 100:2 | 410 | 5 | 99.5 | 9.6 | 88.8 |
| 4 | 100:4 | 410 | 5 | 99.7 | 7.8 | 90.1 |
| 5 | 100:4 | 380 | 5 | 93.2 | 15.6 | 83.5 |
| 6 | 100:8 | 420 | 5 | 99.5 | 4.5 | 91.3 |
| 7 | 100:8 | 450 | 7 | 100 | 2.3 | 90.4 |
| 8 | 100:10 | 410 | 3 | 96.2 | 7.5 | 87.7 |
| 9 | 100:20 | 410 | 8 | 98.9 | 6.9 | 88.2 |

EXAMPLE 10

The procedure of Example 1 was repeated except that the methanol was replaced by ethanol.

The conversion of the phenol was 85%. The selectivity was 16.5% for o-ethylphenol and 80.9% for 2,6-diethylphenol.

EXAMPLE 11

The procedure of Example 1 was repeated except that the phenol was replaced by m-cresol and the reaction was carried out at 430° C.

The conversion of the m-cresol was 100%. The selectivity was 7.2% for 2,3-dimethylphenol, 1.4% for 2,5-dimethylphenol, and 89.4% for 2,3,6-trimethylphenol.

Control 1

Using chromium (III) nitrate nonahydrate alone, a catalyst consisting solely of chromium oxide was prepared in the same manner as described in Example 2. Thereafter, the procedure of Example 2 was repeated.

The conversion of the phenol was 67.4%. The selectivity was 33.6% for o-cresol and 59.7% for 2,6-xylenol.

EXAMPLE 12

Five hundred g. of chromium (III) nitrate nonahydrate, 50 g of tin (II) chloride dihydrate, and 50 g of iron (III) nitrate nonahydrate were dissolved in 15 l of water, and 500 g of urea was added to this solution. The precipitate which was formed by boiling the solution on a heater was separated by filtration, washed with water, and then dried at 120° C. for about 15 hours. The dried precipitate was crushed and adjusted to a particle size of 6–12 mesh. Then, 120 ml of the resulting catalyst (with a Cr:Sn:Fe atomic ratio of 100:28:10) was packed into a stainless steel tubular reactor having an internal diameter of 25 mm. The catalyst was calcined at 460° C. for 3 hours, during which time nitrogen was passed through the reactor. A mixture of phenol and methanol (in a molar ratio of 1:4) was vaporized in a vaporizer kept at 300° C. and then introduced at a rate of 60 g per hour into the reactor having an internal temperature of 360° C. The reaction product was cooled by passing it through a water-cooled condenser and then collected in a dry ice-acetone trap.

The reaction product thus obtained was analyzed by gas chromatography. The conversion of the phenol was 100%. The selectivity based on the amount of phenol converted was 6.8% for o-cresol, 91.5% for 2,6-xylenol, and 0.5% for 2,4,6-trimethylphenol.

EXAMPLE 13-19

Catalysts consisting of chromium oxide, tin oxide, and iron oxide in various Cr:Sn:Fe atomic ratios were prepared in the same manner as described in Example 12. Using these catalysts, various mixtures of phenol and methanol were made to react at different temperatures. The results are summarized in Table 2.

Table 2

| Example No. | Composition of Catalyst (Cr:Sn:Fe Atomic Ratio) | Reaction Temperature (°C.) | Molar Ratio of Methanol to Phenol | Conversion of Phenol (%) | Selection for 2,6-Xylenol (%) |
|---|---|---|---|---|---|
| 13 | 100:2:0.2 | 410 | 5 | 99.4 | 88.5 |
| 14 | 100:4:0.8 | 400 | 5 | 99.8 | 90.7 |
| 15 | 100:8:2 | 380 | 7 | 100 | 92.1 |
| 16 | 100:16:1 | 400 | 5 | 99.7 | 89.9 |
| 17 | 100:16:8 | 370 | 5 | 100 | 92.2 |
| 18 | 100:16:8 | 360 | 7 | 100 | 93.6 |
| 19 | 100:20:5 | 380 | 5 | 100 | 90.9 |

EXAMPLE 20

The procedure of Example 12 was repeated except that the methanol was replaced by isopropanol.

The conversion of the phenol was 81.1%. The selectivity was 21.5% for o-isopropylphenol and 62.1% for 2,6-di-isopropylphenol.

EXAMPLE 21

The procedure of Example 12 was repeated except that the phenol was replaced by m-cresol and the reaction was carried out at 380° C.

The conversion of the m-cresol was 100%. The selectivity was 13.5% for 2,3-dimethylphenol, 2.3% for 2,5-dimetylphenol, and 82.4% for 2,3,6-trimethylphenol.

Controls 2–4

Catalysts consisting solely of chromium oxide and iron oxide in various Cr:Fe atomic ratios were prepared in the same manner as described in Example 12. Thereafter, the procedure of Example 12 was repeated. The results are summarized in Table 3.

Table 3

| Control No. | Composition of Catalyst (Cr:Fe Atomic Ratio) | Conversion of Phenol (%) | Selectivity (%) o-Cresol | 2,6-Xylenol | 2,4,6-Trimethylphenol |
|---|---|---|---|---|---|
| 2 | 100:10 | 74.2 | 32.0 | 64.1 | 1.9 |
| 3 | 100:5 | 71.5 | 35.6 | 59.4 | 2.6 |
| 4 | 100:1 | 70.9 | 44.2 | 54.2 | 1.8 |

EXAMPLE 22

Five hundred g. of chromium (III) nitrate nonahydrate and 20 g of tin (II) chloride dihydrate were dissolved in 10 l of water, and 5% aqueous ammonium was slowly sdded to this solution until its pH reached 7.0%. The precipitated hydrogel was separated by filtration and washed with water. After the addition of 500 ml of N/10 sulfuric acid, the mixture was blended well in a kneader and dried at 120° C. for 5 hours. The dried gel was crushed and adjusted to a particle size of 6–12 mesh. Then, 120 ml of the resulting catalyst (with a Cr:Sn:S atomic ratio of 100:11:2) was packed into a stainless steel tubular reactor having an internal diameter of 25 mm. An electric heater was used to externally heat the reactor through which nitrogen was being passed slowly. Thus, the internal temperature of the reactor was kept at 450° C. for 5 hours and then reduced to 360° C. A mixture of phenol and methanol (in a molar ratio of 1:5) was passed over a preheating bed kept at 250° C. and then introduced into the reactor at a rate of 110 g per hour. The reaction product was cooled by passing it through a water-cooled condenser and then collected in a dry ice-acetone trap.

The product thus obtained was analyzed by gas chromatography. The conversion of the phenol was 99.9%. The selectivity based on the amount of phenol converted was 4.1% for o-cresol and 93.5% for 2,6-xylenol.

EXAMPLE 23

The procedure of Example 22 was repeated except that the methanol was replaced by isopropanol.

The conversion of the phenol was 89.1%. The selectivity was 23.4% for o-isopropylphenol and 68.3% for 2,6-di-isopropylphenol.

EXAMPLES 24–30

Catalysts consisting of chromium oxide, tin oxide, and sulfate radical in various Cr:Sn:S atomic ratios were prepared in the same manner as described in Example 22. Using these catalysts, the reaction was carried out at different temperatures. The results are summarized in Table 4.

Table 4

| Example No. | Composition of Catalyst (Cr:Sn:S Atomic Ratio) | Reaction Temperature (°C.) | Conversion of Phenol (%) | Selectivity (%) | |
|---|---|---|---|---|---|
| | | | | o-Cresol | 2,6-Xylenol |
| 24 | 100:10:1 | 373 | 98.9 | 7.8 | 90.0 |
| 25 | 100:10:2 | 370 | 99.2 | 5.3 | 92.3 |
| 26 | 100:10:10 | 359 | 99.9 | 4.1 | 91.8 |
| 27 | 100:24:2 | 361 | 99.8 | 5.1 | 92.5 |
| 28 | 100:26:12 | 352 | 100 | 3.2 | 91.7 |
| 29 | 100:21:8 | 353 | 98.8 | 6.5 | 93.0 |
| 30 | 100:21:8 | 388 | 99.9 | 2.3 | 93.1 |

EXAMPLE 31

Five hundred g. of chromium (III) nitrate nonahydrate, 50 g of tin (II) chloride dihydrate, and 50 g of iron (III) nitrate nonahydrate were dissolved in 15 l of water, and 500 g of urea was added to this solution. The precipitate which was formed by boiling the solution on a heater was separated by filtration and then washed with water. After the addition of 500 ml of N/10 sulfuric acid, the mixture was blended well in a kneader and dried at 120° C. for about 6 hours. The dried precipitate was crushed and adjusted to a particle size of 6–12 mesh. Then 60 ml of the resulting catalyst (with a Cr:Sn:Fe:S atomic ratio of 100:28:10:2) was packed into a stainless steel tubular reactor having an internal diameter of 25 mm. The catalyst was calcined at 450° C. for 3 hours, during which time nitrogen was passed through the reactor. A mixture of phenol and methanol (in a molar ratio of 1:6) was vaporized by heating at 250° C. and then introduced into the reactor having an internal temperature of 365° C. The reaction product was cooled by passing it through a water-cooled condenser and then collected in a dry ice-acetone trap.

The product thus obtained was analyzed by gas chromatography. The conversion of the phenol was 100%. The selectivity based on the amount of phenol reacted was 3.2% for o-cresol and 94.8% for 2,6-xylenol.

EXAMPLES 32–38

Catalysts consisting of chromium oxide, tin oxide, iron oxide, and sulfate radical in various Cr:Sn:Fe:S atomic ratios were prepared in the same manner as described in Example 31. Using these catalysts, the reaction was carried out at different temperatures. The results are summarized in Table 5.

Table 5

| Example No. | Composition of Catalyst (Cr:Sn:Fe:S Atomic Ratio) | Reaction Temperature (°C.) | Conversion of Phenol (%) | Selectivity (%) | |
|---|---|---|---|---|---|
| | | | | o-Cresol | 2,6-Xylenol |
| 32 | 100:8:1:0.5 | 368 | 99.0 | 7.6 | 90.3 |
| 33 | 100:10:2:1 | 370 | 99.8 | 5.0 | 93.2 |
| 34 | 100:10:5:2 | 363 | 99.9 | 4.1 | 94.4 |
| 35 | 100:19:5:1 | 367 | 99.8 | 4.9 | 93.9 |
| 36 | 100:24:8:5 | 352 | 100 | 5.2 | 92.8 |
| 37 | 100:19:12:10 | 353 | 99.9 | 4.8 | 94.0 |
| 38 | 100:19:16:4 | 388 | 100 | 2.3 | 96.3 |

EXAMPLE 39

Five hundred g. of chromium (III) nitrate nanahydrate, 25 g of tin (II) chloride dihydrate, and 50 g of iron (III) nitrate nonahydrate were dissolved in 15 l of water, and 700 g of urea was added to this solution. The precipitate which was formed by boiling the solution on a heater was separated by filtration and then washed with water. After the addition of 20 millimoles of potassium sulfate dissolved in 200 ml of water, the mixture was blended well in a kneader and dried at 120° C. for about 12 hours. The resulting catalyst had a Cr:Sn:Fe:S atomic ratio of 100:14:10:16. Thereafter, the procedure of Example 31 was repeated.

The conversion of the phenol was 100%. The selectivity based on the amount of phenol reacted was 3.3% for o-cresol and 94.9% for 2,6-xylenol.

EXAMPLE 40

The procedure of Example 31 was repeated except that the methanol was replaced by isopropanol.

The conversion of the phenol was 78.9%. The selectivity was 26.7% for o-isopropylphenol and 70.4% for 2,6-di-isopropylphenol.

EXAMPLE 41

The procedure of Example 31 was repeated except that the phenol was replaced by m-cresol.

The conversion of the m-cresol was 98%. The selectivity was 4.8% for 2,3-dimethylphenol, 0.9% for 2,5-dimethylphenol, and 91.5% for 2,3,6-trimethylphenol.

What is claimed is:

1. In a process for the selective alkylation of the ortho position of a phenolic compound of the formula

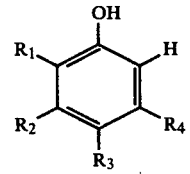

wherein $R_1$, $R_2$, $R_3$ and $R_4$ independently represent hydrogen atoms or saturated aliphatic hydrocarbon radicals having from 1 to 4 carbon atoms, by the catalytic reaction of said phenolic compound with a saturated aliphatic alcohol having from 1 to 4 carbon atoms, in the vapor phase, the improvement which comprises reacting at a temperature of from 250° C. to 550° C. said phenolic compound with said alcohol in a molar ratio ranging from 1:1 to 1:15 in the presence of a catalyst containing chromium oxide and tin oxide and having a Cr:Sn atomic ratio of from 100:0.1 to 100:60.

2. A process as claimed in claim 1 wherein the Cr:Sn atomic ratio ranges from 100:1 to 100:20.

3. A process as claimed in claim 1 wherein the reaction is carried out at a temperature of from 300° C. to 550° C.

4. A process as claimed in claim 1 wherein said catalyst further includes iron oxide, the chromium oxide, the tin oxide and the iron oxide being present in such a proportion as to give a Cr:Sn:Fe atomic ratio ranging from 100:01:0.01 to 100:60:20.

5. A process as claimed in claim 4 wherein the Cr:Sn:Fe atomic ratio ranges from 100:1:0.1 to 100:20:10.

6. A process as claimed in claim 1 wherein the active substance of the catalyst consists essentially of chromium oxide, tin oxide, and sulfate radical.

7. A process as claimed in claim 6 wherein the chromium oxide, the tin oxide, and the sulfate radical are present in such a proportion as to give a Cr:Sn:S atomic ratio ranging from 100:0.1:0.25 to 100:60:20.

8. A process as claimed in claim 7 wherein the Cr:Sn:S atomic ratio ranges from 100:1:0.5 to 100:20:10.

9. A process as claimed in claim 6 wherein the reaction is carried out at a temperature of from 250° C. to 500° C.

10. A process as claimed in claim 1 wherein the active substance of the catalyst consist essentially of chromium oxide, tin oxide, iron oxide, and sulfate radical.

11. A process as claimed in claim 10 wherein the chromium oxide, the tin oxide, the iron oxide, and the sulfate radical are present in such a proportion as to give a Cr:Sn:Fe:S atomic ratio ranging from 100:0.1:0.01:0.25 to 100:60:20:20.

12. A process as claimed in claim 11 wherein the Cr:Sn:Fe:S atomic ratio ranges from 100:1:0.1:0.5 to 100:20:10:10.

13. A process as claimed in claim 12 wherein the reaction is carried out at a temperature of from 250° C. to 500° C.

14. A process for the selective alkylation of the ortho position of a phenolic compound of the formula

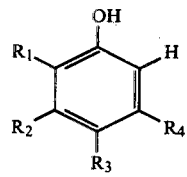

where $R_1$, $R_2$, $R_3$ and $R_4$ independently represent hydrogen atoms or saturated aliphatic hydrocarbon radicals having from 1 to 4 carbon atoms, by reaction of said phenolic compound with a saturated aliphatic alcohol having from 1 to 4 carbon atoms, in the vapor phase, which comprises reacting the phenolic compound with the alcohol in a molar ratio ranging from 1:1 to 1:15 in the presence of a catalyst having an active substance selected from the group consisting of $Cr_2O_3$-$SnO_2$ of a Cr:Sn atomic ratio ranging from 100:0.1 to 100:60, $Cr_2O_3$-$SnO_2$-$Fe_2O_3$ of a Cr:Sn:Fe atomic ratio ranging from 100:0.1:0.01 to 100:60:20, $Cr_2O_3$-$SnO_2$-$SO_4$— of a Cr:Sn:S atomic ratio ranging from 100:0.1:0.25 to 100:60:20 and $Cr_2O_3$-$SnO_2$-$Fe_2O_3$-$SO_4$— of a Cr:Sn:Fe:S atomic ratio ranging from 100:0.1:0.01:0.25 to 100:60:20:20, at a temperature of from 250° C. to 550° C.

15. A process as claimed in claim 14 wherein the mixture is diluted with an inert gas.

16. A process as claimed in claim 14 wherein the reaction is carried out in the presence of water.